Figure 1:
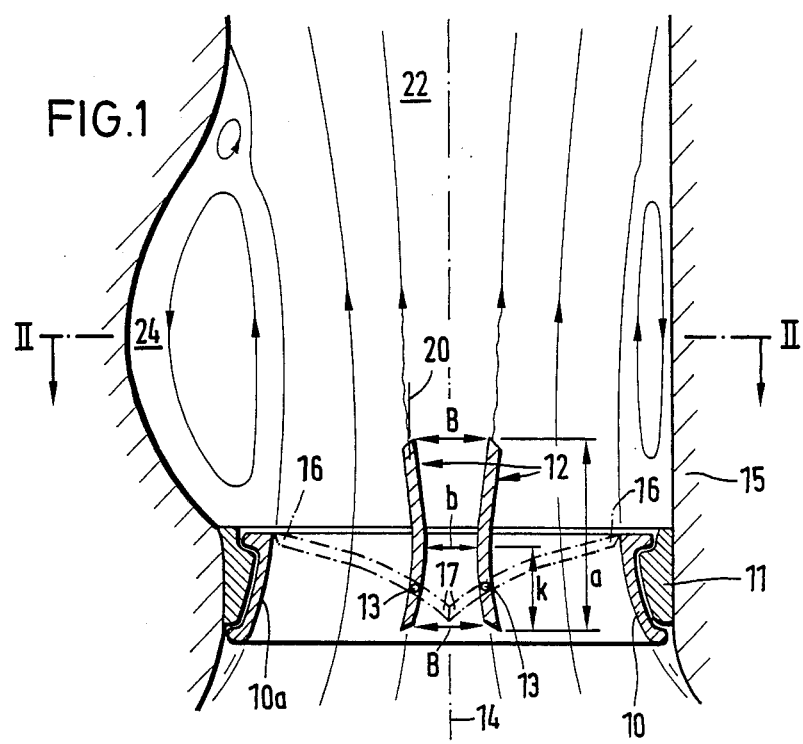

United States Patent [19]

Knoch et al.

[11] Patent Number: 4,846,830

[45] Date of Patent: Jul. 11, 1989

[54] CARDIAC VALVE PROSTHESIS

[75] Inventors: Martin Knoch, Aachen; Helmut Reul, Düren; Günter Rau, Aachen, all of Fed. Rep. of Germany

[73] Assignee: B. Braun Melsungen AG, Melsungen, Fed. Rep. of Germany

[21] Appl. No.: 145,887

[22] Filed: Jan. 20, 1988

[30] Foreign Application Priority Data

Jan. 22, 1987 [DE] Fed. Rep. of Germany ....... 3701704

[51] Int. Cl.$^4$ .............................................. A61F 2/24
[52] U.S. Cl. ...................................................... 623/2
[58] Field of Search ............................................ 623/2

[56] References Cited

U.S. PATENT DOCUMENTS 4,451,937  6/1984  Klawitter .................................. 623/2

FOREIGN PATENT DOCUMENTS 0211576  2/1987  European Pat. Off. ................ 623/2

Primary Examiner—Richard J. Apley
Assistant Examiner—James Prizant
Attorney, Agent, or Firm—Spensley Horn Jubas & Lubitz

[57] ABSTRACT

A cardiac valve prosthesis in which each closing body has a skeleton line which is curved in the area of the swivel axis. The curved area is followed by a rectilinear area, thus causing a linear cross sectional enlargement in the outlet region of the passage formed by the closing bodies. The opening and closing behavior of the cardiac valve becomes more stable, deadwater ares and vortex formation are largely avoided and natural blood flow is substantially undeviated.

8 Claims, 4 Drawing Sheets

CARDIAC VALVE PROSTHESIS

The invention relates to a cardiac valve prosthesis.

Natural cardiac valves are of the tricuspid or biscupid type which, technically speaking, function as nonreturn valves allowing blood to flow unidirectionally, while the counterdirection is blocked. If natural cardiac valves are replaced by mechanical prostheses of the pendulum type or tilting disk type, monocuspid or bicuspid valves are inserted wherein valvular closing bodies in the valve ring fixed by sewing at the respective heart opening are movable by blood pressure or blood flow. However, from a long-term use of such cardiac valve prostheses, serious problems may result for a patient which may entail his lifelong taking of anticoagulants or an interchange of the prosthesis.

For the fluid-mechanical behaviour of the closing body of a cardiac valve prosthesis, its skeleton line is of decisive importance, said skeleton line being meant to refer to the centerline of the closing body cross section extending transversely to the swivel axis. There are known bicuspid cardiac valve prostheses comprising semicircular or semielliptic closing bodies having a rectilinear skeleton line or one which is curved circularly. Further, there are known bicuspid cardiac valve prostheses wherein the closing bodies are curved transversely to the skeleton line in order to increase the cross section of the central opening limited by the two closing bodies without the need of also increasing the most narrow cross section of the resultant channel. The curve in transverse direction to the skeleton line exclusively serves for increasing among three partial passages the central one, and to increase the opening and closing moments. In open position, the closing bodies are curved out of the ring axis towards the ring periphery.

In the known bicuspid cardiac valve prostheses having plane closing bodies, the maximum opening angle at which the closing body hits the abutment is about 85° to the ring discharge plane in order to ensure that, in opened position, the flow firmly presses the valve against the abutment and that, in case of reflux, the safe closing of the closing body is realised. Hence, in the main flowing phase and seen in flow direction, the closing bodies form a diffusor-type cross sectional shape of the central passage. The flow is laterally deviated at the sharp-edged leading edges whereby, in the central partial cross section, a flow separation is caused at said leading edges. Subsequently, the flow again randomly reattaches to the closing bodies, while, behind the other closing body, an extensive wake-flow with a strongly fluctuating vortex formation is produced. This condition may change with each beating cycle. The opening behaviour of the two closing bodies is unequal because of the different pressure distributions. A similar irregular flow behaviour is also typical to closing bodies having a circularly curved skeleton line. In case of said closing bodies which, starting from the narrowest point of the cross section formed between them, are flared in a diffusor-like manner, the flow separates in the region of the cross sectional enlargement.

Flow separations and deadwater areas behind the cardiac valve prostheses in the region of the aorta ascendens are inherent to all closing body designs known hitherto. Due to occurring high shearing stresses, blood may be damaged; by the changing flow conditions, the aortic wall is greatly stressed locally. Further, it is disadvantageous that in the area of the aortic sinuses, deadwater areas are formed from which blood flows insufficiently away thus entailing an increased risk of thrombus formation.

It is an object of the invention to provide a cardiac valve prosthesis wherein a substantially uniform and central flow through the aortic sinuses and the aorta ascendens is ensured, no flow disrupture occurs at the closing bodies in open condition, nor is a substantial deviation of the blood caused either.

The closing bodies of the cardiac valve prosthesis of the invention are so shaped that, in the opening position, they form in the central section a Venturi tube whose diffusor area situated behind the narrowest point, is enlarged linearly in cross section. Said cross sectional enlargement is so small that no flow disrupture may occur. On the other hand, the closing bodies are safely held in the opening position and pressed against their abutments by the flow pressing from the outside against the diverging areas and by the suction developing at the narrowest point of the nozzle cross section behind the swivel axis. The nozzle walls of the nozzle resulting during the open position of the closing bodies are only curved in the converging inlet area while they are of a rectilinear configuration in the diverging outlet area. Seen in flow direction, the narrowest point of the nozzle cross section is behind the swivel axes. Inlet width and outlet width of the nozzle are substantially equal. The minimum possible radius of curvature of the skeleton line on the leading edge side is limited in that, in open position, no flow separation should occur at the closing body surfaces. To this effect, in the leading edge area, the closing bodies may be also of a variable thickness. The skeleton line contour downstream of the point of the narrowest cross section (in the opening position of the closing body) is preferably straight and follows a diffusor opening angle between 3° to 5° to the ring axis so that separations are again excluded.

Contrary to the closing bodies having straight skeleton lines, the opening angle between the chord connecting the closing body ends and the ring discharge plane may be 90°. The required torque for closing, in case of pressure reversal, is caused by the retaining flow in the downstream part of the Venturi nozzle. Upon opening, the overpressure decreasing with the increasing opening angle and being exerted on the concave closing body outsides is supported by the underpressure developing at the site of the narrowest cross section. As a result, the closing bodies are realiably drawn against their abutments.

Due to the cardiac valve prosthesis of the invention in connection with a nozzle-type valve ring whose opening cross section continously (i.e. kinklessly) decreases in flow direction, a valve throughflow without flow separation is possible. Contrary to the monocuspid design, the flow is not deviated from the parallel direction and, because of the minimal flow disturbance, it reattaches to the total circumference of the aorta ascendens already shortly behind the aortic bulbs. The pressure loss is clearly below the lowest pressure loss known hitherto for known mechanical valve prostheses. It may be expected that postoperative treatment with anticoagulants may be reduced to a far extent.

It is one substantial advantage of the additional curve transversely to the skeleton line as specified in claims 6 and 7 that, by maintaining the determined narrowest cross section between the opened closing bodies, the mutual distances between the swivel axes are larger. As a result, the wall-near flow momentum grows in the area of the closing body bearing and the risk of a thrombus accumulation is reduced.

Subclaims 2 to 7 relate to favorable developments and configurations of the invention.

Figure 2:
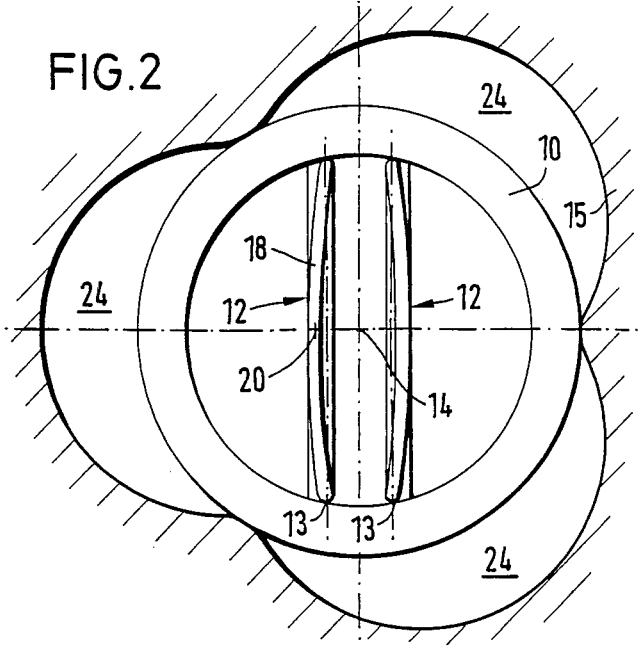
Figure 4:
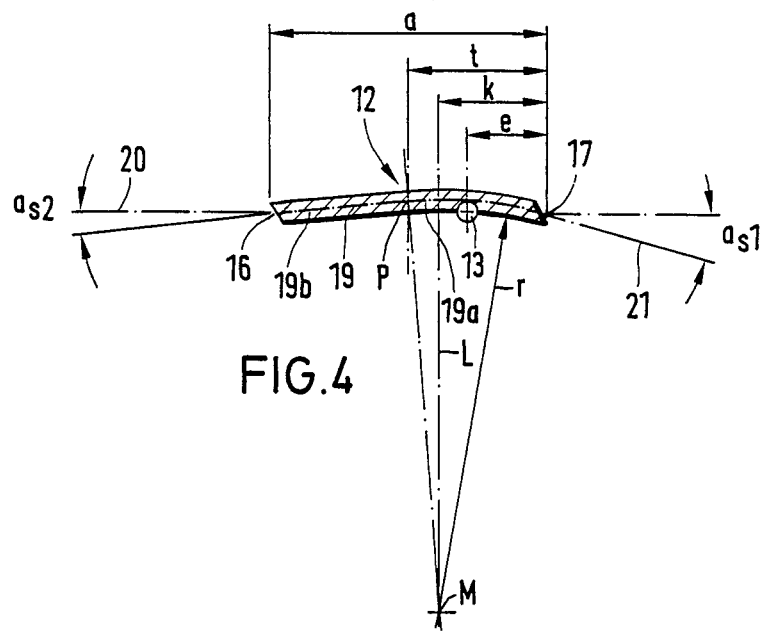
Figure 3:
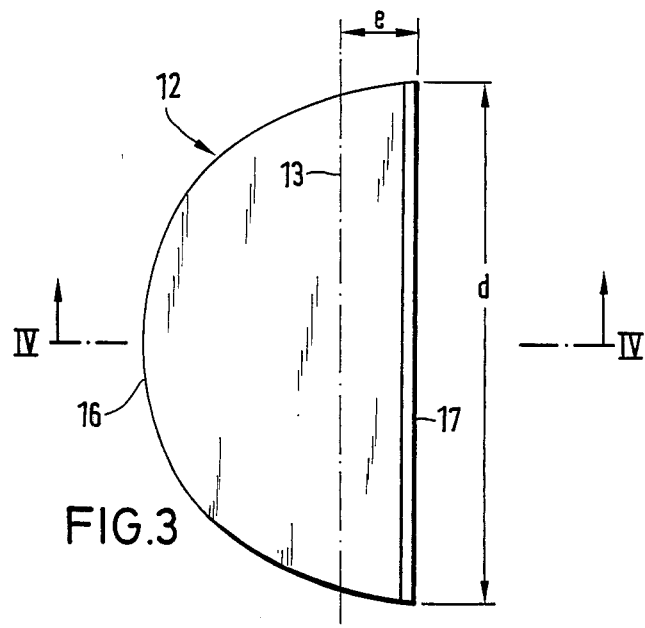
Figure 5:
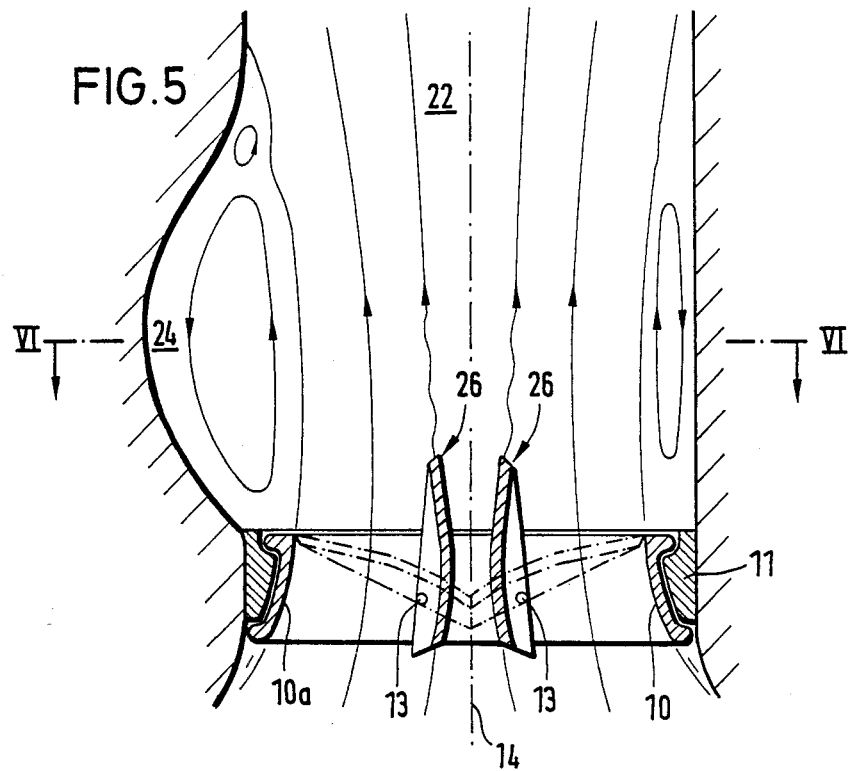
Figure 6:
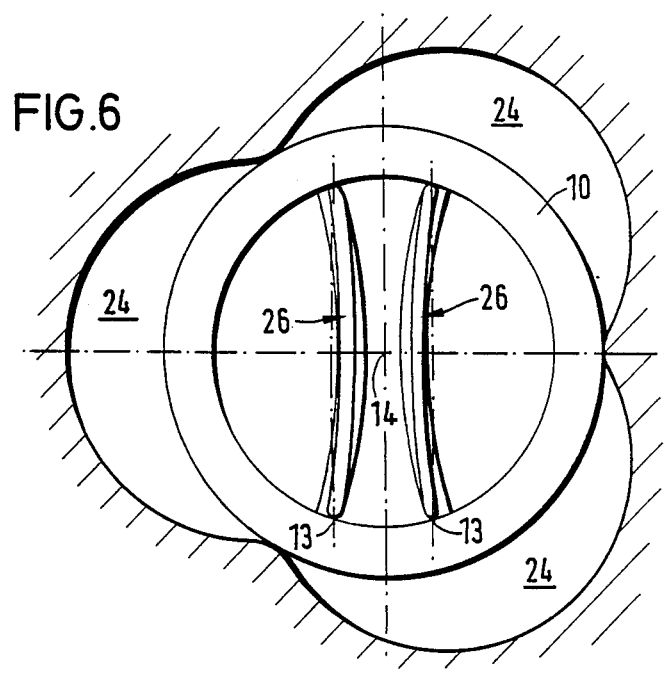
Figure 7:
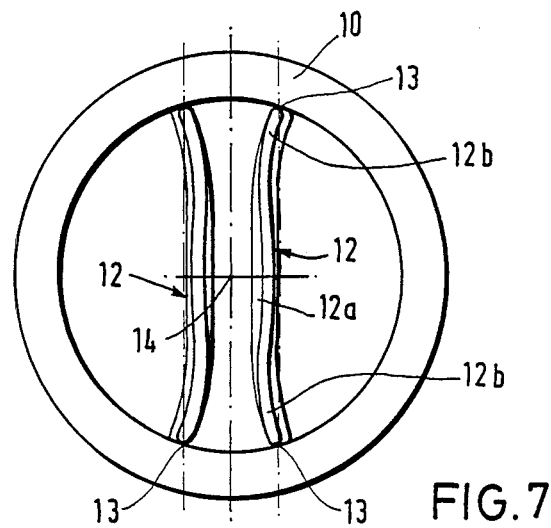
Figure 8:
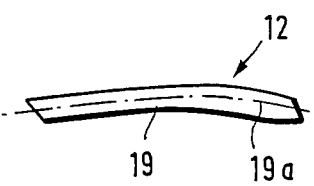

Embodiments of the invention will be explained hereunder in more detail with reference to the drawings in which FIG. 1 is a cross section of an implanted cardiac valve prosthesis, FIG. 2 is a section along line II—II of FIG. 1, FIG. 3 is a view of a closing body, FIG. 4 is a section of the closing body along line IV—IV of FIG. 3 to explain the closing body geometry, FIG. 5 is a second embodiment of the cardiac valve prosthesis in implanted condition, FIG. 6 is a section along line VI-VI of FIG. 5, FIG. 7 is a view similar to FIG. 2 of a cardiac valve prosthesis whose closing bodies 12, in opened condition, form a venturi channel with parallel wall portions, and FIG. 8 is a modified cross sectional shape of a closing body similar to FIG. 4.

The cardiac valve prosthesis of FIGS. 1 to 4 comprises a circular valve ring 10 whose inner area 10a smoothly decreases in flow direction, the valve ring 10 being enclosed by a sewing ring 11 which may be fixed by sewing to the aortic tissue 15. Both closing bodies 12 are pivotally supported in valve ring 10. The swivel axes 13 extending transversely through the ring nearly in the central plane thereof are arranged eccentrically and spaced each equally from the ring axis 14, both swivel axes 13 extending in parallel to each other. Said axes are not physical but geometrical. On them, there are provided at each closing body two bearing pins which, in opposite directions from the closing body edge project and disappear in respective (non-illustrated) bearing recesses of the valve ring 10.

Each closing body 12 consists of a rigid sheet material of a wall thickness preferably uniform at all points. The shape of each closing body 12 is substantially semicircular or semielliptic (FIG. 3). The bevelled arcuate edge 16 adjoins, in closing condition, the inner face 10a of the valve ring while the rectilinear edges 17 of both closing bodies mutually abut at an obtuse angle in the center of valve ring 10 to form a sealing surface. In closed position, each valve wing 12 is bulged in flow direction. In opened position, the valve wings 12 form a Venturi tube whose flow cross section, in flow direction, first decreases to subsequently grow linearly. The narrowest point is downstream of the swivel axes 13. The mutual distance of the closing bodies at the inlet of the Venturi passage is equal to the mutual distance at the outlet.

FIG. 4 shows the course of the skeleton line 19 of a closing body 12. The skeleton line is the center line of the profile which is situated in a plane extending transversely to the swivel axis 13, namely in the transverse central plane of the closing body. In said plane, the structure of the closing body is most developed of all; as the distance from the center plane increases towards the outside, the closing body becomes flatter and flatter, while the center line corresponding to the skeleton line 19 approaches more and more the chord plane.

Portion 19a of the skeleton line 19 situated adjacent to the bearing axis 13 is of an arcuate design. Its course is circular with the radius r about an axis extending in parallel to the swivel axis 13, the latter being more or less in the center of the arcuate portion 19a. The straight portion 19b of a length nearly equal to that of the arcuate portion 19a adjoins the latter.

The length of the chord 20 between edges 17 and 16 is designated with a, while the distance of swivel axis 13 from edge 17 is marked with e. The quotient e:a is preferably 0.15 to 0.25. Angle $\alpha_{s1}$ between the tangent 21 to the end of the arcuate skeleton line portion 19a at the edge 17 and chord 20 is between 5° and 20°, preferably between 10° and 15°. Angle $\alpha_{s2}$ between the straight portion 19b and chord 20 is preferably 3° to 5°. Radius r of the arcuate portion 19a is $$r = \frac{\sin \alpha_{s2}}{1 - \cos(\alpha_{s1} + \alpha_{s2})} \cdot a.$$

The vertical L which traverses towards the chord 20 the center M of the circle of the circular portion 19a intersects chord 20 at a distance k from the edge 17. Point P where portions 19a and 19b abut, is spaced from edge 17 by distance t. The factors k and t are characterized by the following equations:

$$k = r \sin \alpha_{s1} > e$$

$$t = r (\sin \alpha_{s1} + \sin \alpha_{s2}).$$

FIG. 1 shows the closing bodies 12 in opened and in closed positions, the flow lines resulting from the opened position being marked. The cardiac valve prosthesis is provided at the entry of the aorta ascendens 22, the embodiment thus relating to an aortic valve. However, with a corresponding modification of the textile sewing ring 11, the prostheses may be used similarly as a mitral valve. Behind the cardiac valve, three radially arranged aortic sinuses 24 accomodated in the aorta ascendens surround the cusps of the natural trileaflet cardiac valve. If the natural cardiac valve is removed and replaced by the cardiac valve prosthesis, the aortic sinuses 24 influence the blood flow and recirculation areas or deadwater areas may be developed. As shown in FIGS. 1 and 2, the cardiac valve prosthesis is so provided that, in opened position, the closing bodies 12 extend nearly in parallel to one aortic sinus 24. As obvious, the ends 16 and 17 point towards the departing or counter to the arriving flow. The chords 20 traversing the ends 16 and 17 in the skeleton line 19 extend at an angle of 90° to the ring plane so that the entry cross section and the exit cross section of the tube formed between closing bodies 12 are equal. Due to the closing bodies 12, the flow is not substantially deviated or randomly whirled.

In case of opened closing bodies 12, B refers to the distance between edges 17 of the closing body at the nozzle inlet. The distance between the edges 16 at the nozzle outlet is also B. The mutual distance of the closing bodies 12 at the narrowest nozzle point, i.e. at a distance k from the inlet end is b. Therefore, the following standard values are applicable:

$$\frac{b}{a} = 0.20 \text{ to } 0.35$$

$$\frac{b}{B} = 0.65 \text{ to } 0.85.$$

In case of the cardiac valve prosthesis shown in FIGS. 5 and 6, the valve ring 10 is of the same design as that of the first embodiment and also the skeleton line of the closing body 26 corresponds to that of the closing body of the first embodiment. There is only a difference in that each closing body 26 is additionally curved transversely to the plane of the skeleton line which corresponds to the cross sectional plane of FIG. 5. In opened position, the closing bodies are curved from the swivel axes 13 towards the ring axis 4. Due to said curve, in case of a defined mutual minimal distance of the closing bodies, the swivel axes 13 are farther apart from one another to obtain a larger distance from the appertaining skeleton line. If the tube cross section in the skeleton line plane (sectional plane of FIG. 5) is maintained, the tube cross section is increased in total so that the cross section of the central opening is further approximated to the cross sections of the two external openings.

Further, acute angles unfavorable for the wash-out behaviour are avoided at the bearing points between inner ring face and closing body surfaces.

In case of the cardiac valve prosthesis of FIG. 7, the cross sectional shape of the closing bodies 12 in the region of the skeleton line plane is identical to that of the closing body of FIG. 4, each closing body 12 forming transversely to the skeleton line plane a rectilinear central section 12a adjoined by the end sections 12b curved outwardly, in opened position, towards the swivel axis 13. With opened closing bodies, each end section 12b preferably extends at a right angle to the inner face of valve ring 10 against which it abuts. In opening condition, the central sections 12a extend in parallel to each other while end sections 12b of the two closing bodies 12 are divergent. Between the closing bodies 12, there is formed a Venturi passage having parallel wall portions. Said embodiment combines the advantages of the cardiac valves according to FIGS. 1,2 and 5,6, with plenty of scope for conforming the most favorable distance e of the swivel axis 13 from the edge 17 of FIGS. 3 and 4 regardless of the selected tube cross section in the skeleton line plane.

FIG. 8 shows another embodiment of the profile of the closing body in the skeleton line plane. While the wall thickness of the material of the closing body according to FIG. 4 is constant, a varying thickness distribution in the area of the skeleton line portion 19a is used in case of the closing body of FIG. 8. Said varying thickness distribution is provided to avoid flow disruptures at the concave closing body surface, in particular in case that $\alpha_{s1}$ is larger than 15°.

What is claimed is:

1. Cardiac valve prosthesis comprising:
    a valve ring having a ring axis,
    two closing bodies, each of said closing bodies pivotally supported about a respective swivel axis extending transversely and spaced from the ring axis to thereby pivot between an open position and a closed position, each of said closing bodies having a shorter wing section and a longer wing section
    the shorter wing sections of the closing bodies resting against each other in the closed position,
    the longer wing sections of the closing bodies adjoining the valve ring in the closed position,
    the closing bodies, in the open position, defining a central passage of the valve ring, each of said closing bodies further comprising:
    a skeleton line of the cross section of each closing body extending in a plane normal to the swivel axis,
    an arcuate portion extending substantially over half the length of the closing body, and
    a straight portion extending over the residual length of the closing body,
    the arcuate portion being provided near the swivel axis.

2. Cardiac valve prosthesis as defined in claim 1, wherein an angle of 10° to 15° is formed between a line tangent to the end of the arcuate portion and a chord traversing the ends of the skeleton line.

3. Cardiac valve prosthesis as defined in claim 1, wherein an angle of 3° to 5° is formed between the straight portion and a chord traversing the ends of the skeleton line.

4. Cardiac valve prosthesis as defined in claim 1, wherein the swivel axis is provided in the central region of the arcuate portion.

5. Cardiac valve prosthesis as defined in claim 3, wherein, in the open condition, the cord traversing the ends of the skeleton line extends in parallel to the ring axis.

6. Cardiac valve prosthesis as defined in claim 1, wherein each closing body is curved transversely to the plane normal to the swivel axis and towards the ring axis, the halves of each closing body separated by the skeleton line being symmetrical with respect to each other.

7. Cardiac valve prosthesis as defined in claim 6, wherein each closing body comprises a straight central portion and one or more end sections adjioned thereto, the end sections being outwardly curved toward the swivel axis in the open position, and the central sections of both closing bodies forming a Venturi passage having parallel side walls.

8. A cardiac valve prosthesis comprising:
    a valve ring having a ring axis,
    two closing bodies, each closing body pivotally supported about a respective swivel axis extending transversely to and spaced from the ring axis, each closing body further comprising:
    a cross sectional skeleton line extending in a plane normal to the respective swivel axis,
    an arcuate portion near the respective swivel axis and extending substantially over half the length of the closing body, and
    a straight portion extending over the residual length of the closing body.

* * * * *